[19] United States Patent
Weissman et al.

[11] Patent Number: 4,973,555
[45] Date of Patent: Nov. 27, 1990

[54] HUMAN SERINE PROTEASE GENE

[75] Inventors: Irving L. Weissman, Stanford; Howard K. Gershenfeld, Menlo Park, both of Calif.

[73] Assignee: The Board of Trustees of the Leland Stanford Junior University, Stanford, Calif.

[21] Appl. No.: 948,248

[22] Filed: Dec. 31, 1986

Related U.S. Application Data

[63] Continuation-in-part of Ser. No. 860,085, May 6, 1986, abandoned.

[51] Int. Cl.$^5$ .................. C12N 9/64; C12N 9/48; C12N 15/52; C12N 1/21; C12N 5/10; C12N 15/70; C12N 15/74; C12N 15/79
[52] U.S. Cl. .................. 435/226; 435/69.1; 435/70.1; 435/71.1; 435/91; 435/172.1; 435/172.3; 435/240.2; 435/252.3; 435/320; 435/212; 435/213; 536/27; 935/6; 935/9; 935/14; 935/18; 935/22; 935/60; 935/72

[58] Field of Search .............. 435/212, 226, 213, 70.1, 435/69.1, 71.1, 172.1, 172.3, 91, 240.2, 252.3, 320; 935/6, 9, 22, 60, 14, 18, 72; 536/27

[56] References Cited

U.S. PATENT DOCUMENTS 4,783,410 11/1988 Pasternack et al. ................ 435/196

OTHER PUBLICATIONS

Lobe et al., Biochemistry, vol. 27, #18, 6942–6948 (1988).
Pasternack et al., Nature, vol. 314 (1985), 743–746.
Lobe et al., Proc. Natl. Acad. Sci., vol. 83 (1986), 1448–1452.

Primary Examiner—Richard A. Schwartz
Assistant Examiner—Richard C. Peet
Attorney, Agent, or Firm—Bertram I. Rowland

[57] ABSTRACT

Novel human serine proteases are provided characterized by expression in cytotoxic killer cells, being about 25.8kD, and having the amino acid residues of the serine protease charge-relay catalytic mechanism conserved. The proteases can be produced by recombinant DNA technology. The cDNA is also provided.

10 Claims, 3 Drawing Sheets

```
                                   -20
Human  ATG AGG AAC TCC TAT AGA TTT CTG GCA TCC TCT CTC TCA GTT    42
       Met Arg Asn Ser Tyr Arg Phe Leu Ala Ser Ser Leu Ser Val Mouse          ATG AGC AAA GAA ATG AAT GAA ATA CTC TTG AGT
               Met Ser Lys Glu Met Asn Glu Ile Leu Leu Ser -10                              -1
   43  GTC GTT TCT CTC CTG CTA ATT CCT GAA GAT GTC TGT GAA AAA    84
       Val Val Ser Leu Leu Leu Ile Pro Glu Asp Val Cys Glu Lys TGG GAG ATC AAC CTG TCT TCC AAG AGA GGA GGC TGT GAA AGA
       Trp Glu Ile Asn Leu Ser Ser Lys Arg Gly Gly Cys Glu Arg ↓ +1                            +10
   85  ATT ATT GGA GGA AAT GAA GTA ACT CCT CAT TCA AGA CCC TAC   126
       Ile Ile Gly Gly Asn Glu Val Thr Pro His Ser Arg Pro Tyr ATC ATT GGA GGA GAC ACG GTT GTT CCT CAC TCA AGA CCG TAT
       Ile Ile Gly Gly Asp Thr Val Val Pro His Ser Arg Pro Tyr +20
  127  ATG GTC CTA CTT AGT CTT GAC AGA AAA ACC ATC TGT GCT GGG   168
       Met Val Leu Leu Ser Leu Asp Arg Lys Thr Ile Cys Ala Gly ATG GCT CTA CTT AAA CTT AGT TCA AAT ACC ATC TGT GCT GGC
       Met Ala Leu Leu Lys Leu Ser Ser Asn Thr Ile Cys Ala Gly +30                            +40  *
  169  GCT TTG ATT GCA AAA GAC TGG GTG TTG ACT GCA GCT CAC TGT   210
       Ala Leu Ile Ala Lys Asp Trp Val Leu Thr Ala Ala His Cys GCT TTG ATT GAA AAG AAC TGG GTG TTG ACT GCT GCC CAC TGT
       Ala Leu Ile Glu Lys Asn Trp Val Leu Thr Ala Ala His Cys +50
  211  AAC TTG AAC AAA AGG TCC CAG GTC ATT CTT GGG GCT CAC TCA   252
       Asn Leu Asn Lys Arg Ser Gln Val Ile Leu Gly Ala His Ser AAC GTG GGA AAG AGA TCT AAG TTC ATT CTT GGG GCT CAC TCA
       Asn Val Gly Lys Arg Ser Lys Phe Ile Leu Gly Ala His Ser +60                                       +70
  253  ATA ACC AGG GAA GAG CCA ACA AAA CAG ATA ATG CTT GTT AAG   294
       Ile Thr Arg Glu Glu Pro Thr Lys Gln Ile Met Leu Val Lys ATC AAT AAG       GAG CCA GAA CAA CAG ATA TTG ACT GTT AAG
       Ile Asn Lys       Glu Pro Glu Gln Gln Ile Leu Thr Val Lys
```

FIGURE 1a

```
              -28                                     -20
Human   ATG AGG AAC TCC TAT AGA TTT CTG GCA TCC TCT CTC TCA GTT    42
        Met Arg Asn Ser Tyr Arg Phe Leu Ala Ser Ser Leu Ser Val Mouse           ATG AGC AAA GAA ATG AAT GAA ATA CTC TTG AGT
                Met Ser Lys Glu Met Asn Glu Ile Leu Leu Ser -10                                       -1
     43 GTC GTT TCT CTC CTG CTA ATT CCT GAA GAT GTC TGT GAA AAA    84
        Val Val Ser Leu Leu Leu Ile Pro Glu Asp Val Cys Glu Lys TGG GAG ATC AAC CTG TCT TCC AAG AGA GGA GGC TGT GAA AGA
        Trp Glu Ile Asn Leu Ser Ser Lys Arg Gly Gly Cys Glu Arg ↓ +1                                    +10
     85 ATT ATT GGA GGA AAT GAA GTA ACT CCT CAT TCA AGA CCC TAC   126
        Ile Ile Gly Gly Asn Glu Val Thr Pro His Ser Arg Pro Tyr ATC ATT GGA GGA GAC ACG GTT GTT CCT CAC TCA AGA CCG TAT
        Ile Ile Gly Gly Asp Thr Val Val Pro His Ser Arg Pro Tyr +20
    127 ATG GTC CTA CTT AGT CTT GAC AGA AAA ACC ATC TGT GCT GGG   168
        Met Val Leu Leu Ser Leu Asp Arg Lys Thr Ile Cys Ala Gly ATG GCT CTA CTT AAA CTT AGT TCA AAT ACC ATC TGT GCT GGC
        Met Ala Leu Leu Lys Leu Ser Ser Asn Thr Ile Cys Ala Gly +30                                         +40  *
    169 GCT TTG ATT GCA AAA GAC TGG GTG TTG ACT GCA GCT CAC TGT   210
        Ala Leu Ile Ala Lys Asp Trp Val Leu Thr Ala Ala His Cys GCT TTG ATT GAA AAG AAC TGG GTG TTG ACT GCT GCC CAC TGT
        Ala Leu Ile Glu Lys Asn Trp Val Leu Thr Ala Ala His Cys +50
    211 AAC TTG AAC AAA AGG TCC CAG GTC ATT CTT GGG GCT CAC TCA   252
        Asn Leu Asn Lys Arg Ser Gln Val Ile Leu Gly Ala His Ser AAC GTG GGA AAG AGA TCT AAG TTC ATT CTT GGG GCT CAC TCA
        Asn Val Gly Lys Arg Ser Lys Phe Ile Leu Gly Ala His Ser +60                                             +70
    253 ATA ACC AGG GAA GAG CCA ACA AAA CAG ATA ATG CTT GTT AAG   294
        Ile Thr Arg Glu Glu Pro Thr Lys Gln Ile Met Leu Val Lys ATC AAT AAG     GAG CCA GAA CAA CAG ATA TTG ACT GTT AAG
        Ile Asn Lys     Glu Pro Glu Gln Gln Ile Leu Thr Val Lys
```

FIGURE 1b

```
      +80
295  AAA GAG TTT CCC TAT CCA TGC TAT GAC CCA GCC ACA CGC GAA    336
     Lys Glu Phe Pro Tyr Pro Cys Tyr Asp Pro Ala Thr Arg Glu

AAA GCA TTT CCC TAT CCA TGC TAT GAT GAA TAT ACA CGT GAG
     Lys Ala Phe Pro Tyr Pro Cys Tyr Asp Glu Tyr Thr Arg Glu

*                   +90
337  GGT GAC CTT AAA CTT TTA CAG CTG ACG GAA AAA GCA AAA ATT    378
     Gly Asp Leu Lys Leu Leu Gln Leu Thr Glu Lys Ala Lys Ile

GGG GAT CTA CAA CTT GTA CGG CTA AAG AAA AAA GCA ACA GTT
     Gly Asp Leu Gln Leu Val Arg Leu Lys Lys Lys Ala Thr Val

+100                              +110
379  AAC AAA TAT GTG ACT ATC CTT CAT CTA CCT AAA AAG GGG GAT    420
     Asn Lys Tyr Val Thr Ile Leu His Leu Pro Lys Lys Gly Asp

AAC AGA AAT GTG GCT ATC CTT CAC CTA CCT AAA AAG GGA GAT
     Asn Arg Asn Val Ala Ile Leu His Leu Pro Lys Lys Gly Asp

+120
421  GAT GTG AAA CCA GGA ACC ATG TGC CAA GTT GCA GGG TGG GGG    462
     Asp Val Lys Pro Gly Thr Met Cys Gln Val Ala Gly Trp Gly

GAT GTG AAA CCA GGA ACC AGA TGC CGA GTA GCA GGA TGG GGG
     Asp Val Lys Pro Gly Thr Arg Cys Arg Val Ala Gly Trp Gly

+130                                      +140
463  AGG ACT CAC AAT AGT GCA TCT TGG TCC GAT ACT CTG AGA GAA    504
     Arg Thr His Asn Ser Ala Ser Trp Ser Asp Thr Leu Arg Glu

AGA TTT GGC AAT AAG TCA GCT CCC TCT GAA ACT CTG AGA GAA
     Arg Phe Gly Asn Lys Ser Ala Pro Ser Glu Thr Leu Arg Glu

+                          +150
505  GTC AAT ATC ACC ATC ATA GAC AGA AAA GTC TGC AAT GAT CGA    546
     Val Asn Ile Thr Ile Ile Asp Arg Lys Val Cys Asn Asp Arg

GTC AAC ATC ACT GTC ATA GAC AGA AAA ATC TGC AAT GAT GAA
     Val Asn Ile Thr Val Ile Asp Arg Lys Ile Cys Asn Asp Glu

+160
574  AAT CAC TAT AAT TTT AAC CCT GTG ATT GGA ATG AAT ATG GTT    588
     Asn His Tyr Asn Phe Asn Pro Val Ile Gly Met Asn Met Val

AAA CAC TAT AAT TTT CAT CCT GTA ATT GGA CTA AAC ATG ATT
     Lys His Tyr Asn Phe His Pro Val Ile Gly Leu Asn Met Ile

+170                           $    +180
589  TGT GCT GGA AGC CTC CGA GGT GGA AGA GAC TCG TGC AAT GGA    630
     Cys Ala Gly Ser Leu Arg Gly Gly Arg Asp Ser Cys Asn Gly

TGT GCA GGG GAC CTC CGT GGT GGA AAG GAC TCC TGC AAT GGG
     Cys Ala Gly Asp Leu Arg Gly Gly Lys Asp Ser Cys Asn Gly
```

FIGURE 1c

```
              *                      +190
631  GAT TCT GGA AGC CCT TTG TTG TGC GAG GGT GTT TTC CGA GGG    672
     Asp Ser Gly Ser Pro Leu Leu Cys Glu Gly Val Phe Arg Gly

GAT TCT GGC AGC CCT CTG CTA TGT GAT GGT ATT TTG CGA GGC
     Asp Ser Gly Ser Pro Leu Leu Cys Asp Gly Ile Leu Arg Gly

+200                                   +210
673  GTC ACT TCC TTT GGC CTT GAA AAT AAA TGC GGA GAC CCT CGT    714
     Val Thr Ser Phe Gly Leu Glu Asn Lys Cys Gly Asp Pro Arg

ATC ACC TCT TTT GGT GGA GAG     AAG TGT GGA GAT CGC CGA
     Ile Thr Ser Phe Gly Gly Glu     Lys Cys Gly Asp Arg Arg

+220
715  GGG CCT GGT GTC TAT ATT CTT CTC TCA AAG AAA CAC CTC AAC    756
     Gly Pro Gly Val Tyr Ile Leu Leu Ser Lys Lys His Leu Asn

TGG CCT GGT GTC TAT ACT TTC CTC TCA GAT AAA CAC CTC AAT
     Trp Pro Gly Val Tyr Thr Phe Leu Ser Asp Lys His Leu Asn

+230              +234
757  TGG ATA ATT ATG ACT ATC AAG GGA GCA GTT TAA ATAACCGTT      798
     Trp Ile Ile Met Thr Ile Lys Gly Ala Val  *

TGG ATA AAG AAG ATT ATG AAG GGT TCT GTG TAA ATGTATGTC
     Trp Ile Lys Lys Ile Met Lys Gly Ser Val  *

799  TCCTTTCATTTACTGTGGCTTCTTAATCTTTTCACAAATAAAATCAAGTTGG        850

TTTCACTCCATCCCTGTCACTTCTGTGTCTGATCACAAATAAAATCAACTTG
```

HUMAN SERINE PROTEASE GENE

This is a continuation-in-part of U.S. application Ser. No. 860,085, filed May 6, 1986, now abandoned.

BACKGROUND OF THE INVENTION

1. Field of the Invention

The continuing expansion of new tools, protocols, techniques, and reagents has allowed molecular biologists and immunologists to ask novel questions concerning obscure physiological processes and, in many situations, obtain some insight into the components of the process and the manner in which the components operate. Important to the existence of all vertebrates is their ability to defend themselves against pathogens. In mammals, the immune system is divided into a number of different pathways, each pathway having different defense mechanisms, different components, and different modes of regulation.

The killer cells, of which there are many subsets, are able in a restricted or unrestricted manner to kill cells which can be distinguished from normal cells of the host. These cells may arise from viral transfection or transduction, neoplastic transformation, or transplantation from an allogeneic host, where the transplanted tissue or organ has one or more different major histocompatibility (MHC) Class I or minor histocompatibility surface antigens from the host.

There is substantial interest in being able to understand and influence the natural physiological processes. In the case of transplantation, the ability to inhibit graft rejection would greatly increase the success of the transplantation and possibly allow for broader disparity between the MHC antigens of the donor and the recipient. Understanding of the processes by which killer cells select and destroy other cells will aid in an understanding of autoimmune diseases, as well as allow for aiding individuals who are deficient in their immune response.

It is therefore of substantial interest to be able to identify the structural genes, the regulatory regions associated with the structural genes, and the expression products of the structural genes associated with the various immune mechanisms, particularly in humans. One avenue which would have significant beneficial effect in diagnosis and therapy would be the availability of the genes and components of the killer cell lytic process.

2. Description of the Relevant Literature

Polypeptides released from killer cells and their cytoplasmic granules have been implicated in the lytic event of killer cell lysis mechanisms, such polypeptides including serine proteases, toxic lymphokines and pore forming poly-perforins. (Henkart, et al., *J. Exp. Med.* (1984) 160:75: Podack and Konigsberg, ibid (1984) 160:695: Podack, *Immunology Today* (1985) 6:21: Henkart, *Ann. Rev. Immunol.* (1985) 3:31: Martz, *Immunology Today* (1984) 5(9):254.) The inhibition of CTL or NK mediated target cell lysis by low and high molecular weight serine protease inhibitors has been demonstrated. (Wright and Bonavida in *Natural Killer Activity and Its Regulation* (Ed. T. Hoshinu, et al.) Excerpta Medica, Amsterdam, p. 145 (1984) and references cited therein). Hatcher, *J. Immunol.* (1978) 120:665 isolated a cytotoxic serine protease from unstimulated human peripheral blood lymphocytes with an approximate molecular weight of 30 kB. Pasternak and Eisen, *Nature (Lond.)* (1985) 314:743, reported a trypsin-like serine protease of 28 kD specific for CTL cells. Marks, *Science* (1986) 231:1367 describes general theories concerning cell mediated cytotoxicity. See also U.S. patent application Ser. No. 860,085, filed May 6, 1986, which reports a murine killer cell protease.

SUMMARY OF THE INVENTION

Novel DNA sequences are provided which code for human serine proteases characterized by being produced by activated killer cells, having a molecular weight in the range of about 20–30 kD, and having active site "charge relay" residues analogous to other serine proteases. The subject human serine protease acts in conjunction with other components of a killer cell to provide cytolytic capability.

BRIEF DESCRIPTION OF THE DRAWINGS

The FIGURE is a DNA sequence showing a comparison of the amino acid sequence of the subject human protease and a mouse killer-cell protease.

DESCRIPTION OF THE SPECIFIC EMBODIMENTS

Novel compositions and methods are provided related to novel serine proteases produced by human killer cells, where the compositions comprise nucleic acid sequences coding for biologically active fragments of the serine proteases, the serine proteases, and precursors to the serine proteases. Other compositions include nucleic acid sequences joined to other nucleic acid sequences for cloning and expression of such sequences. Also included are poly(amino acid) compositions, which include biologically active fragment of the serine proteases, the serine proteases, precursors to the serine proteases, and conjugates of the various poly(amino acids) to other moieties for a variety of purposes.

The human serine proteases of the subject invention are characterized by being found in various subsets of human killer cells but in substantially lower amounts or being absent in other kinds of cells. The subject serine protease is further characterized by having a polypeptide molecular weight in the range of about 20–30 kD, more usually in the range of about 23–28 kD, and particularly in the range of about 25–26 kD. The serine protease is further characterized by having an active site "charge-relay" with similar spacing and conformation to that of chymotrypsin, namely having histidine, aspartate, and serine spaced approximately as observed with chymotrypsin, as well as having the trypsin specific aspartate in about the same position as trypsin. Spacing here refers to the number of intervening amino acids. Particularly, the His-Asp spacing is about 41–47 amino acids, particularly 44 amino acids, and the Asp-Ser spacing is about 94–100 amino acids, particularly 97 amino acids. The subject serine protease has an Asp residue from about 3–8 amino acids, particularly 6 amino acids, toward the N-terminus from the Ser residue, similar to trypsin. The serine protease is further characterized by being part of the lytic process of killer cells.

The naturally occurring subject serine proteases are found in a number of subsets of killer cells, such as killer T cells, cytotoxic T lymphocytes (CTL), some T helper cells, NK/NC cells, K cells (which use antibodies to target on a foreign cell), and lymphokine activated killer cells (LAK cells). The expression of the serine protease suggests an "activation" gene related to a lysis mechanism.

The subject serine proteases are involved in a system which requires divalent cations, energy sources and which is responsive to inhibition by low and high molecular weight serine protease inhibitors, such as α-2-macroglobulin and soybean trypsin inhibitor.

The subject serine proteases are not found in significant amounts in such cells as normal muscle cells, liver cells, unstimulated peripheral blood lymphocyte cells, and thymus cells, as well as a number of B cell tumor cell lines.

In the FIGURE the amino acid sequence is set forth in comparison with the amino acid sequences of a mouse killer-cell protease. The amino acid homology within the active-enzyme portion of the protein is 71% with 77% homology at the DNA level within the corresponding region. The overall DNA homology is 72% when the complete coding region and the 3' untranslated region are included. An arrow indicates the site of cleavage which generates the active enzyme. The amino acids of the charge-relay system, $His^{41}$, $Asp^{86}$, and $Ser^{184}$, are each marked with a star. The acidic residue $Asp^{178}$, marked with a $, determines substrate specificity for Lys or Arg. The AATAAA polyadenylation consensus sequence is underlined in the 3' noncoding region. The Asn-linked carbohydrate site which occurs at $Asn^{142}$ is marked by a plus.

The amino acids may be sustituted by conservative changes, with non-conservative changes generally being restricted to positions removed from the active site. Groups of amino acids which may be substituted one for the other include G,A: V,I,L: S,T,M: D,E: K,R: N,Q: and F,W,T,H.

Of particular interest is the amino acid region from amino acid 30 to amino acid 70, more particularly from amino acid 40 to amino acid 60. Also of interest is the region from amino acid 90 to amino acid 120, more particularly from amino acid 100 to amino acid 110. Of further interest is the amino acid sequence of from about 190 to 250, more particularly from about 200 to 240, more particularly from about 220 to about 240. Of further interest is a conserved amino acid sequence of at least about 10 amino acids, usually at least about 12 amino acids, and not more than about 30 amino acids, usually not more than about 20 amino acids, included in the fragments indicated above. Peptides consisting of amino acids from these regions of interest will be useful in preparing antibodies that bind and interfere with the active site of the enzyme.

The nucleotide sequence, either the DNA or RNA, more particularly the DNA sequence, encoding the subject serine proteases or active fragments thereof may be used in a variety of ways. Fragments of the serine proteases may be used as probes for detecting the presence of non-mutated or mutated serine proteases present in mammalian cells. Alternatively, the sequences may be used for expression of amino acid fragments having biological activity or extended fragments having enzymatic activity coming within the sequence indicated in the FIGURE. Thus, the various sequences may be used in conjunction with other DNA sequences to provide constructs for cloning or expression of the indicated DNA sequences. Thus the coding sequence will be joined to flanking regions other than the natural flanking regions. The sequence encoding the serine protease will be less than 5 knt (kilonucleotides). usually less than about 2 knt. For expression, the DNA sequences will be joined to regulatory regions and other functional regions other than the natural regions to provide for the production of the desired poly(amino acids), including oligopeptides of from about 8 to 30 amino acids, more usually from about 10 to 20 amino acids, or polypeptides, of at least about 30.amino acids to about 235 amino acids, usually not more than about 233 amino acids, particularly not more than about 232 amino acids, which may code for the entire naturally occurring serine protease.

The DNA constructs in the direction of transcription will usually include a transcriptional initiation region, the open reading frame beginning with the initiation codon (Met) and the desired peptide, followed by the transcriptional termination region. The transcriptional initiation and termination regions will be chosen so as to be functional in the expression host, which may be prokaryotic or eukaryotic, including such hosts as bacteria, e.g., *E. coli*, fungi, e.g, yeast, such as *Saccharomyces, Kluveromyces*, filamentous fungi, such as *Neurospora, Aspergillus*, etc., silkworm cells, mammalian cells, e.g., Chinese hamster ovary cells, hamster kidney cells, etc. For cloning and expression, unicellular organisms are of particular interest.

In addition to the expression construct, there may be one or more markers which allow for selection of hosts containing the expression construct. Markers may include structural genes capable of expression in the host which provide for antibiotic resistance, complementation, plaque formation, or the like.

Where extrachromosomal maintenance is desired, an origin of replication system will be provided, which allows for extrachromosomal maintenance of the expression construct in the host. The extrachromosomal replication system may be derived from plasmids, viruses, chromosomes (centromeres and autonomous replication systems) and the like. In some instances, the expression construct may be introduced into transposons for integration into the host genome. The cells containing the expression construct are grown in an appropriate nutrient medium and depending upon whether the product is secreted, the cells may be lysed and the product isolated by conventional ways or the supernatant isolated and the product extracted.

The subject peptides may be used for a wide variety of purposes. The subject peptides may be used for preparation of polyclonal or monoclonal antibodies. Where only a fragment of the subject serine proteases is employed, the fragment may be joined to an immunogen to provide for an immunogenic product for injection into a vertebrate for the production of antibodies. The immunogenic protein will be foreign to the intended host and one where polyclonal antibodies may or may not be encountered. The immunogens will usually be greater than 30 kD.

Joining of haptenic or antigenic peptides to a larger polypeptide is well known in the art and a variety of linking groups are available, such as formaldehyde, glutaraldehyde, maleimidobenzoic acid, methyldithioacetic acid, Ellman's reagent, or the like. The particular manner in which the polypeptide fragment of the subject serine proteases is joined to the immunogenic protein is not critical to this invention. Convenient immunogenic proteins include bovine serum albumin, tetanus toxoid, keyhole limpet hemocyanin, bovine betaglobulin, and the like.

Various hosts which may be injected with the immunogen include mice, rats, birds, hamsters, or other mammals, e.g., primates such as humans. The manner of injection and obtaining of polyclonal or monoclonal antibodies has been amply described in the literature and need not be described in detail here. Usually, the immunogen will be injected in one or more sites of the host in volumes of about 0.5 to 5 ml with an immunizing effective amount, sufficient to produce a hemagglutinating titer in the range of about 1:32 to 1:256, where one or more injections may be employed at intervals of from about 2 to 4 weeks. Shortly after the last injection, blood may be harvested from the host and the immunoglobulins isolated.

For polyclonal antibodies, the immunoglobulins may be purified by a wide variety of ways, particularly affinity chromatography. For monoclonal antibodies, the spleens may be removed and fused with syngeneic myeloma cells for production of hybridomas, which may be screened for the production of antibodies specific for the desired epitopic site.

The antibodies may be neutralizing or nonneutralizing, depending upon their effect on the activity of the enzyme, the purpose or result of complex formation, and the like.

The antibodies to the subject serine proteases may find use both in vivo and in vitro. For in vivo use, the antibodies may be used for therapeutic purposes for passive immunization to inhibit immune disorders, inhibit graft rejection, and modulating the immune system. In vitro, the antibodies may be used for diagnostic purposes, in detecting the nature of the cell population, for determining pathological lesions, for determining rejection of organ grafts, and for determining the differentiation state of various cells.

The subject human serine proteases and fragments thereof may be used by themselves or in conjunction with other materials as labels in diagnostic assays. In addition, the serine proteases may be used for removing particular cell types from a heterogeneous population of cells. For example, serine protease-containing cells could be removed from bone marrow or other mixture of cells, where cells are susceptible to the lytic cascade or other inhibitory products of NK or CTL cells.

Depending upon the manner in which the subject compositions are to be used, they may be formulated in a variety of ways, being formulated in aqueous media, for example, aqueous buffered media, e.g., phosphate-buffered saline, Tris-buffered solutions, or the like, where the concentrations may vary from about 0.05 mM, to about 5 mM. Other additives may be present, such as protein stabilizers, inert proteins, bacteriostats and bacteriocides, and the like. The particular formulation will be chosen in relation to the particular application.

Formulations may involve additional members of the lytic mechanism for cytotoxicity, such as the precursors of the polyperforins, activators for the subject protease, substrates for the subject protease, and the like. Thus, some or all of the components of the secretory granules of killer cells may be isolated in crude form and used in conjunction with the subject serine protease in substantially pure form. Usually, the subject serine protease can be provided with at least 90% of its native activity, preferably at least about 95% of its native activity.

The subject compositions may be used in a variety of ways. Antibodies may be prepared from fragments of the serine protease or the entire protease which may act to neutralize the enzymatic function of the serine protease. In addition, the serine protease may serve to identify suicide substrates, natural protease inhibitors, substrate transitional state analogs, or other inhibitors, which may serve to neutralize the active site of HF gene products in mammals, so as to block cytotoxic cell functions.

The ability to inhibit the serine protease may serve in the treatment of graft rejection, in the treatment of immune disorders, where the function of killer cells leads to a pathological state, and in the diagnosis of pathological lesions, where the number, type or activity of killer cells may serve as an important pathognomonic sign.

The serine proteases may be used in the development of labeled substrates, e.g., fluoresceinated or umbelliferyl labeled substrates, to serve in the purification of killer cells and natural killer cells, as may be used in therapy, prior to expansion for subsequent reinfusion or in autoimmune disorders for removal of cells by plasmaphoresis. In addition, by preparing antibodies to the zymogen peptide or the junction of the zymogen peptide and the active serine protease, the antibodies may serve as a diagnostic tool for determining the frequency of blood cells or tissue cells which are in the killer cell set. In addition, the serine protease by itself or in combination with the other members of the cytolytic process of T-cells, including components of the secreted granules, may be used for in vitro and in vivo lysis of cells, permitting a powerful biological purification method. The human serine protease can also serve to identify transition state analogs and other small molecular weight protease inhibitors that are preferentially specific to this enzyme's active site, thereby identifying molecules capable of inhibiting T-cell and/or NK cytotoxicity.

The following examples are offered by way of illustration and not by way of limitation.

EXAMPLE

A cDNA phage library was prepared from human peripheral blood lymphocytes (PBL) after 4 days of stimulation with phytohemagglutinin (PHA). This cDNA library was made in λgt10 by modifications of a cDNA procedure described by Huynh *DNA Cloning Techniques: A Practical Approach* (Ed. D. Glover) IRL PRESS, Oxford (1984). The two modifications were (1) the replacement of all phenol-chloroform extractions with spermine precipitation as described by Hoops et al., *Nucl. Acid Res.* (1981) 9:5493, and (2) the replacement of the Biogel A-50m column with 1% to 2% agarose horizontal gel electrophoresis for the purpose of removing the excess EcoRI linkers and size fractionating ds cDNA. The ds cDNAs were size selected initially for lengths greater than 0.5 kb and subsequently for lengths greater than 0.95 kb. The selected agarose slices were electroeluted in dialysis bags (Smith, *Methods in Enzymology* (1980) 65:371) and spermine precipitated. All RNAs for the cDNA libraries, Northerns and S1 analysis were prepared by guanidinium thiocyanate extraction (Chirgwin et al., *Biochem.* (1979) 18:5294) and polyA selected with oligo-dT cellulose.

$2 \times 10^5$ recombinant phage plaques of the PHA stimulated PBL cDNA library were screened with the mouse serine protease cDNA. The probe was prepared by nick translation as described by Meinkoth and Wahl, supra, and the cDNA libraries were plated at a density of approximately 50,000 pfu/150 cm plate as described by Hunyh et al., supra. One phage was picked and rescreened through two additional rounds of hybridization, yielding a plaque-purified clone. The purified lambda phage contained a 1.3 kilobase (kb) EcoRI cDNA insert encoding the human equivalent of the mouse serine protease HF gene (designated HuHF). By Northern analysis, this cDNA hybridized to a 1.3 kb polyA-RNA species present in human CTL cells generated in a four-day alloreactive mixed lymphocyte culture and in Jurkat tumor cells. By Northern analysis, the RNA was not detected in normal human muscle, liver, tonsil, or lymphoid tissue. Furthermore, no RNA could be detected in the following tumors: KB cell (a nasopharyngael carcinoma), RPMI 4265 and NA (B cell tumors), and SS II (T cell). From RNA dot blot experiments, the RNA was detectable in three human CTL alloreactive cloned lines (AI5.1, AMSB.3, AMW.6), in non-stimulated, cell sorted Leu 11+NK and Leu 11−Leu 4+T cell large granular lymphocytes (LGL) from PBL.

The nucleotide sequence was completely determined on both strands, except for the 5 prime most 400 nucleotides, yielding a single open reading frame (see FIG. 1). In FIG. 1, the nucleotide sequence and amino acid translation of the human cDNA is aligned with the mouse sequence. The amino acid sequence is numbered sequentially from the predicted amino terminus of the putative active enzyme. An arrow indicates a putative site of cleavage, generating the active enzyme predicted based on homology alignments. The amino acids of the charge relay system, $His^{41}$, $Asp^{86}$ and $Ser^{184}$, are each marked with a star. The acidic residue $Asp^{178}$, marked with a $, determines the substrate's specificity by analogy with other serine proteases. The AATAAA polyadenylation consensus sequence is underlined in the 3' noncoding region. A potential Asn-linked carbohydrate site occurs at $Asn^{142}$ marked by +.

By protein sequence homology, the DNA sequence encodes an active serine protease of 234 amino acids, with a non-glycosylated, polypeptide molecular weight of approximately 25.8 kD. The active enzyme is probably preceded by a zymogen peptide by analogy with other serine proteases, cleaving c-terminal to Lys (−1). The amino acids of the serine protease charge-relay catalytic mechanism are conserved, with the His and Asp being separated by 44 amino acids and the Asp and Ser being separated by 97 amino acids as compared to a separation in chymotrypsin of 44 and 92, respectively. The HF serine protease contains an $Asp^{178}$ residue equivalent to the $Asp^{189}$ of trypsin, suggesting trypsin-like substrate specificity.

The amino acid composition is shown in Table 1 for the uncleaved protease and the cleaved, active protein.

TABLE 1

| COMPLETE HuHF PROTEIN | | | | |
|---|---|---|---|---|
| The uncleaved protein contains 262 amino acids: | | | | |
| Ala | 13 | (5.0) | Leu | 27 | (10.3) |
| Arg | 15 | (5.7) | Lys | 19 | (7.3) |
| Asn | 15 | (5.7) | Met | 7 | (2.7) |
| Asp | 13 | (5.0) | Phe | 5 | (1.9) |
| Cys | 10 | (3.8) | Pro | 13 | (5.0) |
| Gln | 4 | (1.5) | Ser | 18 | (6.9) |
| Glu | 11 | (4.2) | Thr | 14 | (5.3) |
| Gly | 22 | (8.4) | Trp | 4 | (1.5) |
| His | 7 | (2.7) | Tyr | 7 | (2.7) |
| Ile | 18 | (6.9) | Val | 20 | (7.6) |
| End | 0 | (0.0) | | | |
| Acidic | (Asp + Glu) | | 24 | (9.2) |
| Basic | (Arg + Lys) | | 34 | (13.0) |
| Aromatic | (Phe + Trp + Tyr) | | 16 | (6.1) |
| Hydrophobic | (Aromatic + Ile + Leu + Met + Val) | | 88 | (33.6) |

TABLE 1-continued

| | | | | |
|---|---|---|---|---|
| Molecular Weight = 28972. | | | | |
| ACTIVE HuHF PROTEIN | | | LIMITS: | 29   262 |
| The cleaved protein contains 234 amino acids: | | | | |
| Ala | 12 | (5.1) | Leu | 22 | (9.4) |
| Arg | 13 | (5.6) | Lys | 18 | (7.7) |
| Asn | 14 | (6.0) | Met | 6 | (2.6) |
| Asp | 12 | (5.1) | Phe | 4 | (1.7) |
| Cys | 9 | (3.8) | Pro | 12 | (5.1) |
| Gln | 4 | (1.7) | Ser | 13 | (5.6) |
| Glu | 9 | (3.8) | Thr | 14 | (6.0) |
| Gly | 22 | (9.4) | Trp | 4 | (1.7) |
| His | 7 | (3.0) | Tyr | 6 | (2.6) |
| Ile | 17 | (7.3) | Val | 16 | (6.8) |
| End | 0 | (0.0) | | | |
| Acidic | (Asp + Glu) | | 21 | (9.0) |
| Basic | (Arg + Lys) | | 31 | (13.2) |
| Aromatic | (Phe + Trp + Tyr) | | 14 | (6.0) |
| Hydrophobic | (Aromatic + Ile + Leu + Met + Val) | | 75 | (32.1) |
| Molecular Weight = 25820 | | | | |

The cleaved, active human HF protein shares 71% of its amino acids with its mouse homologue. This is reflected in a 77% DNA similarity. The overall DNA similarity is 72% when the complete coding region and the 3' untranslated region are included.

All publications and patent applications cited in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A DNA sequence encoding a novel human serine protease or a fragment of said serine protease having at least 90% of protease activity of said serine protease joined to other than a natural flanking region, said serine protease being characterized by being found in granules of activated human killer T cells, having a molecular weight in the range of about 20–30 kD, and being capable of being a member of the cytolytic activity of cytolytic T cells and having a cDNA sequence as set forth in the FIGURE.

2. A DNA sequence according to claim 1, which is a cDNA sequence.

3. A DNA sequence according to claim 1, joined at the 5'-terminus to a transcriptional initiation region other than the natural transcriptional initiation region.

4. A DNA sequence according to claim 3, joined at its 3'-terminus to a transcriptional termination region.

5. A DNA sequence according to claim 4, joined to a replication system functional in a unicellular organism.

6. A DNA sequence according to claim 4, joined to a replication system functional in a mammalian cell.

7. A cell containing a DNA sequence according to claim 4, wherein said transcriptional initiation and termination regions are functional in said cell.

8. A unicellular micro-organism cell containing a DNA sequence according to claim 6.

9. A method for producing a serine protease or fragment thereof characterized by having at least 90% of the protease activity of the serine protease which comprises:
  growing cells according to claim 7, whereby said DNA is expressed; and
  isolating said serine protease or fragment thereof characterized by having at least 90% of the protease activity of the serine protease, free of cellular debris.

10. A method according to claim 9, wherein said cells are unicellular micro-organism cells.

* * * * *

UNITED STATES PATENT AND TRADEMARK OFFICE
CERTIFICATE OF CORRECTION

PATENT NO. : 4,973,555

DATED : November 27, 1990

INVENTOR(S) : Weissman et al.

It is certified that error appears in the above-indentified patent and that said Letters Patent is hereby corrected as shown below:

Column 1, line 3

This invention was made with U.S. Government support under contract 5P01AI19512 awarded by the National Institutes of Health. The Government has certain rights in this invention.--

Signed and Sealed this

Fourth Day of April, 1995

Attest:

BRUCE LEHMAN

*Attesting Officer*              *Commissioner of Patents and Trademarks*